United States Patent [19]

Honda

[11] Patent Number: 5,750,563
[45] Date of Patent: May 12, 1998

[54] PREPARATION FOR EPIDERMIS

[75] Inventor: Shinsuke Honda, Onojo, Japan

[73] Assignee: Sansho Seiyaku Co., Ltd., Onojo, Japan

[21] Appl. No.: 538,380

[22] Filed: Oct. 3, 1995

Related U.S. Application Data

[63] Continuation of Ser. No. 238,628, May 5, 1994, abandoned.

[30] Foreign Application Priority Data

Oct. 28, 1993 [JP] Japan ................................. 5-270972

[51] Int. Cl.⁶ ........................................................ A61K 31/35
[52] U.S. Cl. ............................ 514/460; 514/27; 514/32; 514/23
[58] Field of Search ............................ 514/460, 27, 32, 514/23

[56] References Cited

U.S. PATENT DOCUMENTS

| | | | |
|---|---|---|---|
| 4,847,074 | 7/1989 | Hatae et al. | 424/62 |
| 4,956,353 | 9/1990 | Dowd | 514/65 |

FOREIGN PATENT DOCUMENTS 5-154916  12/1980  Japan ........................ A61K 31/35

OTHER PUBLICATIONS

Gabor et al 111CA:186892f, 1989.
Saito et al 111CA:140525k 1989.
Merk Index 10th Ed. 1983, #'s 1883, 7760 7441, 4216, 3132.
Zhang, 110CA:199009c, 1989.
Mota et al 103CA:189375k 1985.
Bissett et al 112CA:145346h 1990.
Remington Pharm Sci 17th Ed, 1985, p. 777.
Merck Index 10th Ed 1983 #8569.

*Primary Examiner*—Russell Travers
*Attorney, Agent, or Firm*—Armstrong, Westerman, Hattori, McLeland & Naughton

[57] ABSTRACT

A preparation for epidermis containing kojic acid and/or its derivative, which has improved preparation stability, is provided. The preparation stability is imparted by adding to the preparation at least one member selected from the group consisting of alcohols and polyphenols.

1 Claim, No Drawings

PREPARATION FOR EPIDERMIS

This application is a continuation of application Ser. No. 08/238,628 filed May 5, 1994, now abandoned.

BACKGROUND OF THE INVENTION

This invention relates to a preparation for epidermis containing kojic acid and/or its derivative and an ultraviolet light absorbent, which further contains at least one member selected from the group consisting of alcohols and polyphenols for improving stability of kojic acid and/or its derivative contained in the preparation.

As typical forms of preparation for epidermis, there are illustrated O/W (oil-in-water) emulsions and W/O (water-in-oil) emulsions, which are different from each other in water-to-oil composition ratio and physical properties but are both homogeneous preparations wherein oil phase or aqueous phase are stably emulsified and dispersed with the aid of a surfactant.

Kojic acid and its derivatives the inventor has long studied are known as useful agents having various excellent properties, as disclosed in Japanese Unexamined Patent Publication No. S55-157509, Japanese Examined Patent Publication Nos. S56-18569, S58-22151, S58-22152, S58-34446, S60-7961, S60-9722 and S60-10005, Japanese Unexamined Patent Publication No. S60-137253, Japanese Examined Patent Publication Nos. S61-10447 and S61-60801, Japanese Unexamined Patent Publication No. S62-5909, Japanese Examined Patent Publication Nos. S62-3820 and S63-27322, Japanese Unexamined Patent Publication No. H1-132502 and Japanese Examined Patent Publication No. H5-30422.

However, kojic acid and its derivatives (hereinafter these being in some cases merely referred to as "kojic acids") are also known as agents which themselves have difficulty in acquiring stability. Particularly when the kojic acids are incorporated in the aforementioned O/W emulsion or W/O emulsion, it requires a highly sophisticated technique to design a proper formulation. Hence, it has been a pressing subject with respect to formation of a preparation containing the kojic acids to develop a technique which provides the kojic acids-containing prepatation with enough stability to stand severe distributive machinery without giving unpleasant feeling upon application thereof to skin.

In the case of compounding the kojic acids in various preparations for epidermis, they are under the condition of being likely to be exposed to ultraviolet light to varying degrees which can be an external cause of their coloration or decomposition. Thus, it has been conducted to compound an ultraviolet light absorbent in a proper amount for depressing damages by irradiation with ultraviolet light.

Examples thereof are illustrated in, for example, Japanese Unexamined Patent Publication Nos. S62-108804 and s64-83008 and Japanese Examined Patent Publication No. H4-46924.

Many of such ultraviolet light absorbents have a problem with solubility and separate out in the preparation, and fail to fully exhibit their ultraviolet light-absorbing ability, leading to a deteriorated stability of kojic acid.

In order to overcome this defect, solubilizing agents have properly been used. However, the use of oily solubilizing agent in a large amount causes a problem of giving an unpleasant feeling such as sticking feeling upon application to skin.

In addition, it is also known that stability of kojic acids is also influenced by heat. This problem of influence by heat has not so far been solved.

Further, nonionic surfactants, which are properly used as surfactants upon forming a preparation containing kojic acids for external application in view of depressing coloration, giving a pleasant feeling upon application and being harmless to skin, have weaker emulsifying power in comparison with ionic surfactants and suffer decrease in emulsifying power in the presence of a highly polar ingredient or by the influence of pH level. Therefore, in the kojic acid-containing preparation which is usually adjusted to 4 to 5 in pH, incorporation of a highly polar ultraviolet light absorbent causes the problem of deteriorating emulsion stability with time.

SUMMARY OF THE INVENTION

It is, therefore, an object of the present invention to provide a preparation for epidermis which solves the above-described problems with the conventional kojic acid-containing preparation, i.e., which does not suffer separation of the ultraviolet light absorbent and has improved stability with time to coloration and decomposition of kojic acid by, particularly, heat and which is formed by adding at least one member selected from the group consisting of alcohols and polyphenols to a preparation for external application containing kojic acid and/or its derivative.

Other objects, features and advantages of the present invention will become apparent from the detailed description of the preferred embodiments of the invention to follow.

DETAILED DESCRIPTION OF THE PREFERRED EMBODIMENTS OF THE INVENTION

As the kojic acid (5-hydroxy-2-hydroxymethyl-γ-pyrrone) to be used in the present invention as a first ingredient, a pure product of 5-hydroxy-2-hydroxymethyl-γ-pyrrone, a fermentation liquor containing kojic acid as a major component and being obtained by cultivating a known bacterium strain capable of yielding kojic acid, a concentrate of the fermentation liquor, a product obtained by extracting kojic acid from the fermentation liquor and crystallizing the extract, and the like.

As the kojic acid derivatives, those which are disclosed in, for example, Japanese Examined Patent Publication No. S60-10005, H1-45472 and H3-74229, and esterified products of kojic acid and kojic acid derivatives wherein sugars are bound to the —$CH_2OH$ group at 2-position of kojic acid disclosed in, for example, Japanese Examined Patent Publication No. S58-22151 and S58-22152 may be used alone or in combination of two or more.

The kojic acid and/or its derivative is compounded in the preparation in an amount of 0.001 to 10% by weight, preferably 0.1 to 5% by weight, based on the total amount of the preparation for external application.

The ultraviolet light absorbents to be used in the present inventon as a second ingredient are not particularly limited. Preferred examples thereof include benzophenone derivatives such as hydroxybenzophenone, hydroxybenzophenonesulfonic acid, sodium hydroxymethoxybenzophenonesulfonate and dihydroxydimethoxybenzophenone; salicylic acid derivatives such as ethylene glycol salicylate, homomenthyl salicylate and phenyl salicylate; urocanic acid and ethyl urocanate; cinnamic acid derivatives such as 2-ethylhexyl p-methoxycinnamate and octyl methoxycinnamate; p-aminobenzoic acid derivatives such as glyceryl p-aminobenzoate and 2-ethylhexyl p-dimethylaminobenzoate; dibenzoylmethane derivatives such as 4-tet-butyl-4'-methoxydibenzoylmethane; and benzotriazole derivatives such as 2-(2-hydroxy-5-methylphenyl)benzotriazole. These compounds may be used alone or in combination of two or more. In addition, other known animal or vegetable extracts having ultraviolet light-absorbing ability may properly be used alone or in combination.

Amounts of these ultraviolet light absorbents are somewhat varied depending upon the kind thereof but, usually, they are used in an amount of 0.001 to 10% by weight, preferably 0.1 to 5% by weight, based on the total amount of the preparation for external application.

As the alcohols to be used in the present invention as a third ingredient, lower alcohols such as ethanol, propanol and isopropanol; higher alcohols such as octyldodecanol, olive oil alcohol, oleyl alcohol, stearyl alcohol, cetostearyl alcohol, decyltetradecanol, hexyldecanol, jojoba alcohol, myristyl alcohol and lauryl alcohol; polyhydric alcohols such as alkylene (containing 15 to 18 carbon atoms) glycol, alkylene (containing 20 to 30 carbon atoms) glycol, ethylene glycol, highly polymerized polyethylene glycol,diglycerin, dipropylene glycol, hexylene glycol, polyethylene glycol 200, polyethylene glycol 300, polyethylene glycol 400, polyethylene glycol 600, polyethylene glycol 1000, polyethylene glycol 1500, polyethylene glycol 4000, polyethylene glycol 6000, polyethylene glycol 20000, polypropylene glycol 400 and polypropylene glycol 1200; sugaralcohols such as fruit sugar, xylitol, D-xylose, sorbitol, D-sorbitol, glucose, multitol, maltose, D-mznnitol and amylolytic sugaralcohol; and polyhydric alcohol alkyl ethers such as isostearyl glyceryl ether, ethylene glycol ethyl ether, ethylene glycol methyl ether, ethylene glycol monobutyl ether, chimyl alcohol, diethylene glycol ethyl ether, diglyceryl oleyl ether and batyl alcohol are illustrated as preferable examples.

As the polyphenols, pyrogallol; phloroglucinol; catechins such as catechin, epicatechin, gallocatechin, catechin gallate, gallocatechin gallate, epicatechin gallate, epigallocatechin gallate and epigallocatechin; glucogallin; proanthocyanidin; gallic acid; gallic acid esters such as propyl gallate, isoamyloctyl gallate and dodecyl gallate; flavones such as rutin, quercetin, quercetagin, quercetagetin and gossypetin; penta-O-galloyl glucose; tannic acid; various tannins such as gallotannin, ellagitannin and condensed tannins extracted from astringent Japanese persimmon or tea; and shikimic acid are illustrated as preferable examples, which may be used alone or in combiation of two or more.

Amounts of the third ingredient somewhat varies depending upon the kind thereof but, usually, they are addded in an amount of 0.001 to 20% by weight, preferably 0.1 to 10% by weight, based on the total amount of the preparation.

The above-described first to three ingredients may be formed into a preparation for external application in a known manner. Such preparation does not suffer separation of the ultraviolet light absorbent, thus being a stable emulsion preparation having good stability with time, in which the kojic acids show improved stability to coloration and decomposition with time. In particular, addition of the third ingredient serves to markedly improve stability of the kojic acids to heat.

Needless to say, form of the preparation of the present invention is not limited to the emulsion type such as O/W emulsion and W/O emulsion, but may be a transparent type by properly selecting the ingredients. In addition, the present invention may also be applicable as a fundamental technique for forming multi-layer emulsion preparations such as W/O/W or O/W/O emulsions or microcapsule preparations.

The preparation of the present invention for epidermis is not particularly limited as to application form, and may be widely used in a known application form of medicines, quasi-drugs and cosmetics such as cataplasm, plaster, paste, cream, ointment, aerosol, emulsion, lotion, essence, pack, gel, powder, foundation, suncare, bath salts, and the like.

In forming the preparation of the present invention, various known and conventionally used effective ingredients may optionally be incorporated as the case demands in amounts not spoiling the objects of the present invention. Examples of such known effective ingredients include capillary vasodilators such as carpronium chloride, cepharanthine, vitamin E, vitamin E nicotinate, nicotinic acid, nicotinic acid amide, benzyl nicotinate, ginger tincture and chili tincture; coolers such as camphor, mentol and peppermint oil; antimicrobial agents such as hinokitiol, benzalkonium chloride and undecylenic acid; anti-inflammatory agents such as adrenal cortical hormone,є-aminocaproic acid, lysozyme chloride, glycyrrhizin and allantoin; fairness-imparting agents such as ascorbic acid and arbutin; various extracts of animal or vegetable origin such as placenta extract, liver extract, lithospermum root extract and extract of culture liquor of lactic acid bacteria.

In addition to the known effective ingredients, various known additives such as humectants, antiseptics, antioxidants, chelating agents, pH-adjusting agents, perfumes and colorants may also be used, as well as a base ingredient such as a fat and oil, within a range of not spiling the objects of the present invention in the above-described application forms of medicines, quasi-drugs and cosmetics.

The present invention is now described in more detail by reference to experiments and formulations which, however, are not construed to be limitative at all.

Experiment 1

Preparation stability test

Method of experiment:

Various creams (pH: about 4.5) were prepared according to the formulations shown in Table 1. After placing them in 4-ounce candle bottle, they were stored for 2 months under the severe condition of 50° C. while irradiating with ultraviolet light. After 2 months, color difference (ΔE) was measured (using a color-difference meter, Z-1001DP, made by Nihon Denshoku Kogyo). In this occasion, observation of change in appearance (separation of the ultraviolet light absorbent and stability of the emulsion), measurement of residual ratio of kojic acid (using HPLC according to the conventional method and being calculated taking the initial value at the start of the test as 100), and evaluation of application feeling were also conducted.

Results of the experiment:

As is shown in Table 1, the preparations in accordance with the present invention suffered no separation of the ultraviolet light absorbent and showed an extremely good emulsion stability. Coloration or decomposition of kojic acid contained in the preparations due to heat was not observed, and application feeling was kept good.

TABLE 1-1

| Name of Ingredient | Examples | | | | | | | |
|---|---|---|---|---|---|---|---|---|
| | 1 | 2 | 3 | 4 | 5 | 6 | 7 | 8 |
| 1. Octyldodecanol | 5.00 | 5.00 | 2.00 | — | — | — | — | — |
| 2. Polyethylene glycol 400 | — | 2.00 | — | — | — | — | 2.00 | — |
| 3. Alkylene (15) glycol | — | — | 5.00 | — | 0.50 | — | — | — |
| 4. Sorbitol | — | — | — | 0.50 | — | — | — | — |
| 5. Isostearyl glyceryl ether | — | — | — | — | 1.50 | — | — | — |
| 6. Epigallocatechin gallate | — | — | — | — | — | 0.50 | — | — |
| 7. Shikimic acid | — | — | — | — | — | — | 1.50 | — |
| 8. Isopropanol | — | — | — | — | — | — | — | 3.00 |
| 9. Kojic acid | 1.00 | 1.00 | 1.00 | 1.00 | 1.00 | 1.00 | 1.00 | 1.00 |
| 10. Oxybenzon | 1.50 | — | 0.80 | — | — | — | — | — |
| 11. 4-tert-Butyl-4'-methoxy-dibenzoyl-methane | — | 1.00 | 0.50 | — | — | — | 0.20 | — |
| 12. Glyceryl p-aminobenzoate | — | — | — | 0.20 | — | — | 0.10 | 1.50 |
| 13. Ethylene glycol salicylate | — | — | — | — | 1.00 | — | — | — |
| 14. Octyl methoxycinnamate | — | — | — | — | — | 0.50 | — | 0.10 |
| 15. Bees wax | 4.50 | 4.50 | 4.50 | 4.50 | 4.50 | 4.50 | 4.50 | 4.50 |
| 16. Vaseline | 2.80 | 2.80 | 2.80 | 2.80 | 2.80 | 2.80 | 2.80 | 2.80 |
| 17. Jojoba oil | 7.00 | 7.00 | 7.00 | 7.00 | 7.00 | 7.00 | 7.00 | 7.00 |
| 18. Natural vitamin E | 0.04 | 0.04 | 0.04 | 0.04 | 0.04 | 0.04 | 0.04 | 0.04 |
| 19. Polyoxyethylene cetyl ether (25 E.O.) | 1.50 | 1.50 | 1.50 | 1.50 | 1.50 | 1.50 | 1.50 | 1.50 |
| 20. Polyoxyethylene stearyl ether (20 E.O.) | 0.70 | 0.70 | 0.70 | 0.70 | 0.70 | 0.70 | 0.70 | 0.70 |
| 21. Carboxyvinyl polymer | 0.08 | 0.08 | 0.08 | 0.08 | 0.08 | 0.08 | 0.08 | 0.08 |
| 22. Sodium dl-Pyrrolidone carboxylate | 6.00 | 6.00 | 6.00 | 6.00 | 6.00 | 6.00 | 6.00 | 6.00 |
| 23. Disodium edetate | 0.02 | 0.02 | 0.02 | 0.02 | 0.02 | 0.02 | 0.02 | 0.02 |
| 24. Citric acid | *1 | *1 | *1 | *1 | *1 | *1 | *1 | *1 |
| 25. Sodium citrate | *1 | *1 | *1 | *1 | *1 | *1 | *1 | *1 |
| 26. Purified water | *2 | *2 | *2 | *2 | *2 | *2 | *2 | *2 |
| Results of the tests: Appearance *3 | no | no | no | no | no | no | no | no |
| *4 | ◉ | ◉ | ◉ | ◉ | ◉ | ◉ | ◉ | ◉ |
| Color difference (ΔE) | 3.0 | 2.3 | 2.6 | 2.2 | 2.3 | 2.5 | 1.9 | 2.6 |
| Evaluation of feeling upon application (*5) *6 | ◉ | ◉ | ◉ | ◉ | ◉ | ◉ | ◉ | ◉ |
| *7 | ◉ | ◉ | ◉ | ◉ | ◉ | ◉ | ◉ | ◉ |
| *8 | ◉ | ◉ | ◉ | ◉ | ◉ | ◉ | ◉ | ◉ |

*1: slight amount
*2: enough amount to make the total amount 100% by weight
*3: Separation of ultraviolet light absorbent
*4: Emulsion state (no separation)
◉ : good; Δ: partly separated; X: separated
*5: Standard of evaluation:
◉ : good; o : almost no problem; Δ: slight problem; x: bad
*6: rough feel
*7: sticky feel
*8: fitness to skin

TABLE 1-2

| Name of Ingredient | Comparative Examples | | | | | | | | |
|---|---|---|---|---|---|---|---|---|---|
| | 1 | 2 | 3 | 4 | 5 | 6 | 7 | 8 | 9 |
| 1. Octyldodecanol | — | — | — | — | — | — | — | — | — |
| 2. Polyethylene glycol 400 | — | — | — | — | — | — | — | — | — |
| 3. Alkylene (15) glycol | — | — | — | — | — | — | — | — | — |
| 4. Sorbitol | — | — | — | — | — | — | — | — | — |
| 5. Isostearyl glyceryl | — | — | — | — | — | — | — | — | — |
| 6. Epigallocatechin gallate | — | — | — | — | — | — | — | — | — |
| 7. Shikimic acid | — | — | — | — | — | — | — | — | — |
| 8. Isopropanol | — | — | — | — | — | — | — | — | — |

TABLE 1-2-continued

| Name of Ingredient | Comparative Examples | | | | | | | | |
|---|---|---|---|---|---|---|---|---|---|
| | 1 | 2 | 3 | 4 | 5 | 6 | 7 | 8 | 9 |
| 9. Kojic acid | 1.00 | 1.00 | 1.00 | 1.00 | 1.00 | 1.00 | 1.00 | 1.00 | 1.00 |
| 10. Oxygenzon | — | 1.50 | — | 0.80 | — | — | — | — | — |
| 11. 4-tert-Butyl-4'-methoxy-dibenzoyl-methane | — | — | 1.00 | 0.50 | — | — | — | 0.20 | — |
| 12. Glyceryl p-amino-benzoate | — | — | — | — | 0.20 | — | — | 0.10 | 1.50 |
| 13. Ethylene glycol salicylate | — | — | — | — | — | 1.00 | — | — | — |
| 14. Octyl methoxycinnamate | — | — | — | — | — | — | 0.50 | — | 0.10 |
| 15. Bees wax | 4.50 | 4.50 | 4.50 | 4.50 | 4.50 | 4.50 | 4.50 | 4.50 | 4.50 |
| 16. Vaseline | 2.80 | 2.80 | 2.80 | 2.80 | 2.80 | 2.80 | 2.80 | 2.80 | 2.80 |
| 17. Jojoba oil | 7.00 | 7.00 | 7.00 | 7.00 | 7.00 | 7.00 | 7.00 | 7.00 | 7.00 |
| 18. Natural vitamine E | 0.04 | 0.04 | 0.04 | 0.04 | 0.04 | 0.04 | 0.04 | 0.04 | 0.04 |
| 19. Polyxoyethylene cetyl ether (25 E.O.) | 1.50 | 1.50 | 1.50 | 1.50 | 1.50 | 1.50 | 1.50 | 1.50 | 1.50 |
| 20. Polyoxytheylene stearyl ether (20 E.O.) | 0.70 | 0.70 | 0.70 | 0.70 | 0.70 | 0.70 | 0.70 | 0.70 | 0.70 |
| 21. Carboxyvinyl polymer | 0.08 | 0.08 | 0.08 | 0.08 | 0.08 | 0.08 | 0.08 | 0.08 | 0.08 |
| 23. Sodium dl-Pyrrolidone carboxylate | 6.00 | 6.00 | 6.00 | 6.00 | 6.00 | 6.00 | 6.00 | 6.00 | 6.00 |
| 23. Disodium edetate | 0.02 | 0.02 | 0.02 | 0.02 | 0.02 | 0.02 | 0.02 | 0.02 | 0.02 |
| 24. Citric acid | *1 | *1 | *1 | *1 | *1 | *1 | *1 | *1 | *1 |
| 25. Sodium citrate | *1 | *1 | *1 | *1 | *1 | *1 | *1 | *1 | *1 |
| 26. Purified water | *2 | *2 | *2 | *2 | *2 | *2 | *2 | *2 | *2 |
| Resilts of the tests  Appearance *3 | — | no | yes | yes | yes | yes | yes | yes | yes |
| *4 | Δ | x | x | x | x | x | x | x | x |
| Color difference | 9.1 | 8.5 | 7.7 | 7.9 | 10.3 | 7.2 | 8.6 | 8.1 | 6.5 |
| Evaluation *6 | ○ | ○ | ○ | x | x | x | x | x | x |
| of feeling *7 | Δ | x | x | Δ | Δ | Δ | Δ | x | x |
| upon application (*5) *8 | Δ | Δ | x | Δ | x | Δ | x | x | Δ |

*1: slight amount
*2: enough amount to make the total amount 100% by weight
*3: Separation of ultraviolet light absorbent
*4: Emulsion state (no separation)
◎ : good; Δ: partly separated; X: separated
*5: Standard of evaluation:
◎ : good; ○ : almost no problem; Δ: slight problem; x: bad
*6: rough feel
*7: sticky feel
*8: fitness to skin Formulation examples of the present invention are shown below.

Formulation example 1 [Cream (1)]

| | (% by weight) |
|---|---|
| 1. Kojic acid | 1.00 |
| 2. Hydroxybenzenesulfonic acid | 0.50 |
| 3. Mannitol | 2.00 |
| 4. Polyethylene glycol 400 | 3.00 |
| 5. Polyoxyethylene cetyl ether (25 E.O.) | 5.00 |
| 6. Stearic acid | 5.00 |
| 7. Avocado oil | 1.00 |
| 8. Almond oil | 10.00 |
| 9. Solution of sodium dl-pyrrolidonecarboxylate | 5.00 |
| 10. p-Hydroxybenzoic acid ester | 0.20 |
| 11. Disodium edetate | 0.01 |
| 12. Purified water to make | 100.00 |

Formulation example 2 [Cream (2)]

| | (% by weight) |
|---|---|
| 1. Kojic acid | 5.00 |
| 2. 4-tert-Butyl-4'-methoxydibenzoylmethane | 0.50 |
| 3. Jojoba alcohol | 1.00 |
| 4. Sorbitol | 3.00 |
| 5. Epicatechin gallate | 0.50 |
| 6. Dimethylsiloxane-methyl (polyoxyethylene-polyoxypropylene copolymer) | 3.00 |
| 7. Jojoba oil | 7.00 |
| 8. Decamethylcyclopentasiloxane | 3.00 |
| 9. Octamethylcyclotetrasiloxane | 3.00 |
| 10. Dimethylpolysiloxane | 5.00 |
| 11. Natural vitamin E | 0.04 |
| 12. 1% Solution of sodium hyaluronate | 2.00 |
| 13. Carrageenan | 1.00 |
| 14. Disodium edetate | 0.01 |
| 15. Purified water to make | 100.00 |

Formulation example 3 [Emulsion (1)]

| | (% by weight) |
|---|---|
| 1. Kojic acid | 4.00 |
| 2. 2-Ethylhexyl p-methoxycinnamate | 2.00 |
| 3. Polyethylene glycol 4000 | 3.00 |
| 4. Octyl dodecanol | 3.00 |
| 5. Polyoxyethylene cetyl ether (25 E.O.) | 0.50 |
| 6. Polyoxyethylene oleyl ether (20 E.O.) | 1.00 |
| 7. Stearic acid | 0.50 |
| 8. Shea butter | 0.50 |
| 9. Avocado oil | 4.00 |
| 10. p-Hydroxybenzoic acid ester | 0.20 |
| 11. Quince seed extract | 5.00 |
| 12. Xanthane gum | 0.14 |

-continued

| | (% by weight) |
|---|---|
| 13. Disodium edetate | 0.01 |
| 14. Purified water to make | 100.00 |

Formulation example 4 [Emulsion (2)]

| | (% by weight) |
|---|---|
| 1. Kojic acid | 0.50 |
| 2. Ethylene glycol salicylate | 0.10 |
| 3. Octyl methoxycinnamate | 2.00 |
| 4. Batyl alcohol | 3.50 |
| 5. Shikimic acid | 2.00 |
| 6. Coconut oil fatty acid monoethanolamide | |
| 7. Stearic acid | 0.50 |
| 8. Myristic acid | 0.50 |
| 9. Avocado oil | 4.00 |
| 10. Natural vitamin E | 0.04 |
| 11. p-Hydroxybenzoic acid ester | 0.20 |
| 12. Sodium hyaluronate | 5.00 |
| 13. Xanthane gum | 0.14 |
| 14. Disodium edetate | 0.01 |
| 15. Purified water to make | 100.00 |

Formulation Example 5 [Lotion]

| | (% by weight) |
|---|---|
| 1. Kojic acid glucoside | 7.00 |
| 2. 4-tert-Butyl-4'-methoxydibenzoylmethane | 2.00 |
| 3. 2-Ethylhexyl p-methoxycinnamate | 0.05 |
| 4. Ethylene glycol ethyl ether | 3.00 |
| 5. Polyoxyethylene cetyl ether (60 E.O.) | 5.00 |
| 6. Ginseng extract | 2.00 |
| 7. Japanese chirate extract | 0.50 |
| 8. p-hydroxybenzoic acid ester | 0.10 |
| 9. Ascorbic acid | 0.10 |
| 10. Sodium citrate | 0.30 |
| 11. 5% Solution of elastin hydrolyzate | 4.00 |
| 12. Disodium edetate | 0.01 |
| 13. Purified water to make | 100.00 |

Formulation example 6 [Cream pack]

| | (% by weight) |
|---|---|
| 1. Ethyl kojate | 2.00 |
| 2. 4-tert-butyl-4'-methoxy-dibenzoylmethane | 0.50 |
| 3. Decyltetradecanol | 2.00 |
| 4. Polyethylene glycol 1500 | 5.00 |
| 5. Stearic acid diethanolamide | 5.00 |
| 6. Stearic acid | 5.00 |
| 7. Myristic acid | 0.50 |
| 8. Coconut oil | 15.00 |
| 9. Natural vitamin E | 0.04 |
| 10. p-Hydroxybenzoic acid ester | 0.20 |
| 11. Solution of sodium dl pyrrolidonecarboxylate | 5.00 |
| 12. Disodium edetate | 0.01 |
| 13. Purified water to make | 100.00 |

Formulation example 7 [Ointment]

| | (% by weight) |
|---|---|
| 1. Kojic acid | 1.00 |
| 2. Hydroxybenzenesulfonic acid | 0.10 |
| 3. Phenyl salicylate | 0.40 |
| 4. Sodium hydroxymethoxybenzophenonesulfonate | 1.00 |
| 5. Isoamyloctyl gallate | 2.00 |
| 6. Coconut oil faty acid monoethanolamide | 5.00 |
| 7. Vasline | 10.00 |
| 8. Stearic acid | 5.00 |
| 9. Oleic acid | 1.00 |
| 10. Olive oil | 10.00 |
| 11. p-Hydroxybenzoic acid ester | 0.20 |
| 12. Carrageenan | 5.00 |
| 13. Disodium edetate | 0.01 |
| 14. Purified water to make | 100.00 |

Formulation example 8 [Cataplasm]

| | (% by weight) |
|---|---|
| 1. Kojic acid fructoside | 0.50 |
| 2. Glyceryl p-aminobenzoate | 4.00 |
| 3. Rutin | 1.00 |
| 4. Stearic acid diethanolamide | 3.00 |
| 5. Polyacrylic acid | 27.00 |
| 6. Licorice extract (ethanol extract) | 0.10 |

-continued

| | (% by weight) |
|---|---|
| 7. Scutellaria root extract (aqueous extract) | 0.05 |
| 8. Disodium edetate | 0.05 |
| 9. Sodium polyacrylate | 7.00 |
| 10. Aluminum chloride | 0.30 |
| 11. Conc. glycerin | 20.00 |
| 12. Titanium oxide | 4.00 |
| 13. Purified water to make | 100.00 |

Formulation example 9 [Essence]

| | (% by weight) |
|---|---|
| 1. Kojic acid | 1.00 |
| 2. Urocanic acid | 0.50 |
| 3. 2-Ethylhexyl p-methoxycinnamate | 1.00 |
| 4. Isopropanol | 0.50 |
| 5. Benzyl alcohol | 0.05 |
| 6. Xylose | 1.50 |
| 7. Coconut oil fatty acid monoethanolamide | 2.00 |
| 8. Stearic acid | 0.50 |
| 9. Linolenic acid | 0.50 |
| 10. Avocado oil | 2.00 |
| 11. Turtle oil | 3.00 |
| 12. Natural vitamine E | 0.04 |
| 13. p-Hydroxybenzoic acid ester | 0.20 |
| 13. 1% Aqueous solution of carboxyvinyl polymer | 5.00 |
| 15. Xanthane gum | 0.14 |
| 16. Disodium edetate | 0.01 |
| 17. Purified water to make | 100.00 |

It has been confirmed that the above-described Formulation Examples 1 to 9 provide preparations having the same satisfactory results as are shown in Table 1.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A method of preventing separation of the ultraviolet light absorbent from a preparation for epidermis containing kojic acid or a derivative thereof, a nonionic surfactant and an ultraviolet light absorbent, and discoloration or decomposition of kojic acid or its derivative in the preparation, which comprises adding to the preparation:

a catechin selected from the group consisting of pyrogallol, phrologlycine, catechin, epicatechin, gallocatechin, catechin gallate, gallocatechin gallate, epicatechin gallate, epigallocatechin gallate, and epigallocatechin; or a flavone selected from the group consisting of glucogallin, proanthocyanidin, gallic acid, propyl gallate, isoamyloctyl gallate, dodecyl gallate, rutin, quercetin, quercetagin and gossypetin; or a polyphenol selected from the group consisting of penta-O-galloyl glucose, tannic acid, gallotannin, ellagitannin and condensed tannins extracted from astringent Japanese persimmon or tea.

* * * * *